(12) United States Patent
Lechner-Fish

(10) Patent No.: US 6,776,025 B2
(45) Date of Patent: Aug. 17, 2004

(54) CARRIER GAS PRE-HEAT SYSTEM FOR GAS CHROMATOGRAPH

(75) Inventor: Teresa Lechner-Fish, Katy, TX (US)

(73) Assignee: Daniel Industries, Inc., Houston, TX (US)

( * ) Notice: Subject to any disclaimer, the term of this patent is extended or adjusted under 35 U.S.C. 154(b) by 0 days.

(21) Appl. No.: 10/062,200

(22) Filed: Oct. 29, 2001

(65) Prior Publication Data

US 2003/0079523 A1 May 1, 2003

(51) Int. Cl.⁷ .................. G01N 30/26; G01N 30/30; G01N 30/32
(52) U.S. Cl. .............. 73/23.41; 73/23.42; 73/23.25; 73/23.26
(58) Field of Search ............... 73/23.41, 23.42, 73/23.25, 23.26; 96/101, 105; 95/89, 99, 114, 115

(56) References Cited

U.S. PATENT DOCUMENTS

| | | | | |
|---|---|---|---|---|
| 3,041,869 A | * | 7/1962 | Spracklen et al. | 73/23.41 |
| 3,778,975 A | * | 12/1973 | Deans | 96/105 |
| 3,779,066 A | * | 12/1973 | Fore et al. | 73/23.25 |
| 3,935,097 A | * | 1/1976 | Roof | 210/659 |
| 4,035,168 A | * | 7/1977 | Jennings | 73/864.85 |
| 4,095,455 A | * | 6/1978 | Karas et al. | 73/23.24 |
| 4,096,734 A | * | 6/1978 | Khayat | 73/23.41 |
| 4,133,640 A | * | 1/1979 | Clinton et al. | 436/85 |
| 4,159,894 A | * | 7/1979 | Hu | 73/23.41 |
| 4,300,393 A | * | 11/1981 | Stearns | 73/863.11 |
| 4,772,296 A | * | 9/1988 | Potts | 95/87 |
| 4,805,441 A | * | 2/1989 | Sides et al. | 73/23.25 |
| 4,872,334 A | * | 10/1989 | Watanabe | 73/23.24 |
| 5,083,450 A | * | 1/1992 | Grindstaff | 73/23.25 |
| 5,205,845 A | * | 4/1993 | Sacks et al. | 73/23.42 |
| 5,252,109 A | * | 10/1993 | Munari et al. | 95/87 |
| 5,322,627 A | * | 6/1994 | Berger et al. | 210/656 |
| 5,402,668 A | * | 4/1995 | Murakami et al. | 73/23.42 |
| 5,922,106 A | * | 7/1999 | Mowry et al. | 73/23.41 |
| 5,970,803 A | * | 10/1999 | Staples et al. | 73/23.41 |

* cited by examiner

*Primary Examiner*—Michael Cygan
(74) *Attorney, Agent, or Firm*—Conley Rose, P.C.

(57) ABSTRACT

The invention is a gas chromatograph that includes a mechanism to heat the carrier gas to a temperature higher than that of the columns through which it flows. The carrier gas may be temperature programmed to achieve much the same results as the known technique of temperature programming the column.

15 Claims, 19 Drawing Sheets

2207 Prior Art

Packed Column

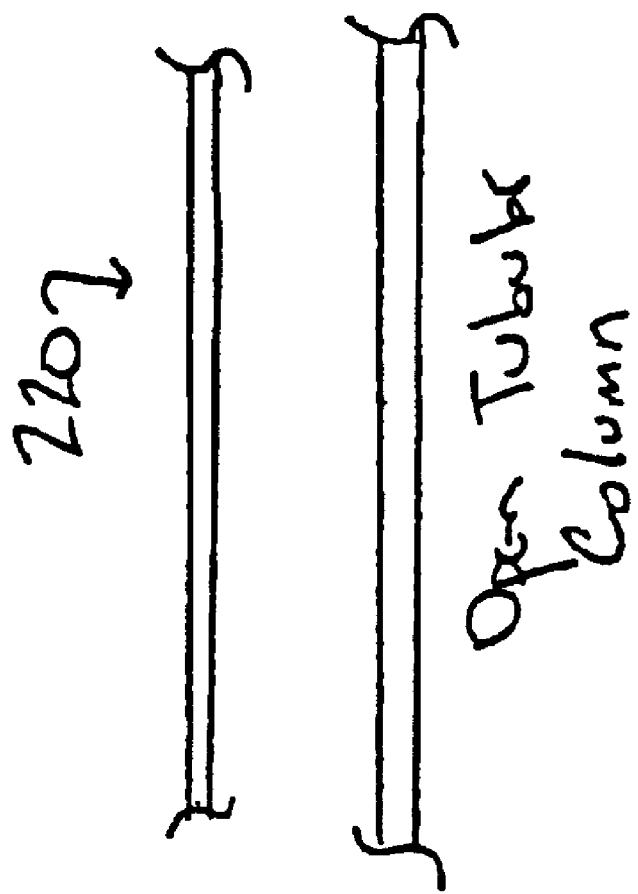

OFF
Prior Art

ON
Prior Art

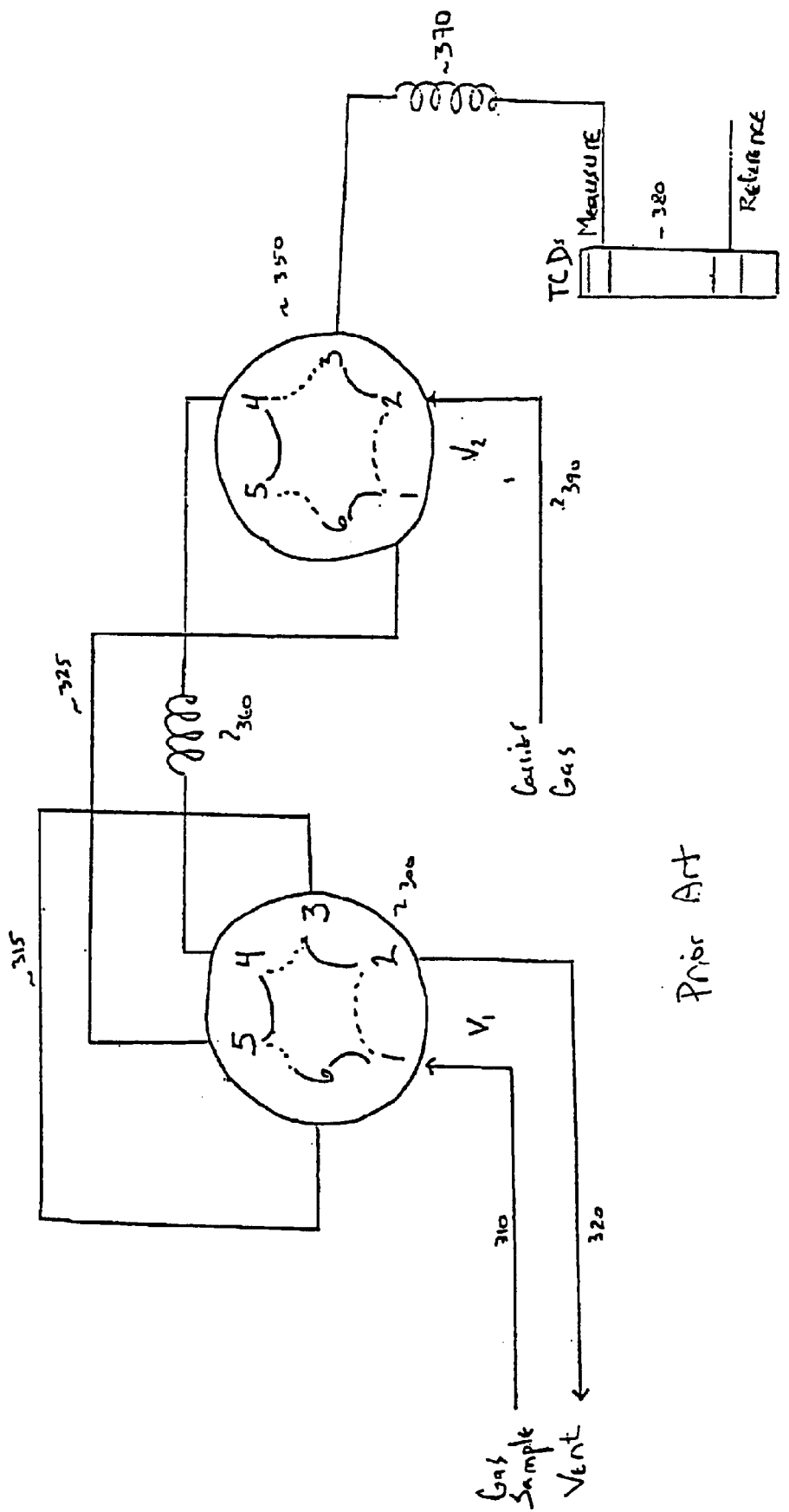

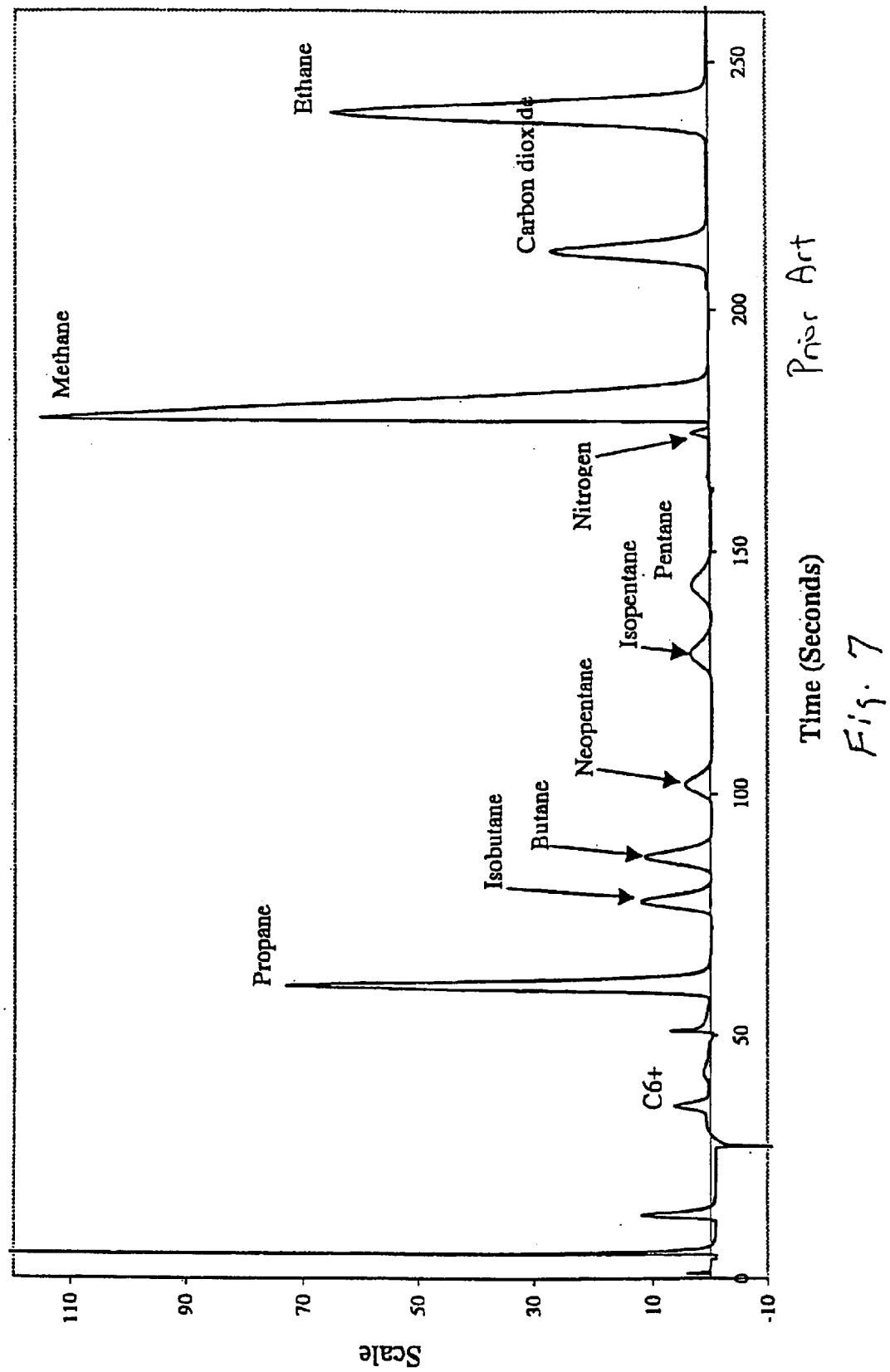

CARRIER GAS PRE-HEAT SYSTEM FOR GAS CHROMATOGRAPH

CROSS-REFERENCE TO RELATED APPLICATIONS

Not Applicable.

STATEMENT REGARDING FEDERALLY SPONSORED RESEARCH OR DEVELOPMENT

Not Applicable.

BACKGROUND OF THE INVENTION

The field of process chromatography is concerned with analyzing gas samples flowing through a process pipeline. A sample from a gas pipeline may be taken by use of a sample probe or other sampling device, which then provides the sample to a gas chromatograph. The gas chromatograph separates the sample into its individual components, using a variety of detectors to analyze the concentration of the resulting component bands in the sample. In the oil and gas industry, the knowledge of what fluid is being transported by the pipeline is useful for a variety of purposes, such as source identification and custody transfer.

FIG. 1 shows a known gas chromatograph system (not to scale). Gas flows through a process pipeline 110, a sample of which is taken by a sample probe 120 prior to being introduced to gas chromatograph (GC) 100. The gas sample may be filtered and heat traced generally along tubing 130 before flowing into gas chromatograph 100. Heating may be required for gases that may condense into a part gas, part liquid flow at cooler temperatures. After being analyzed by the gas chromatograph, the gas sample is either returned into the process pipeline 110, or vented to the atmosphere. As used herein, the term gas chromatograph is being used in its broad sense, to include what is traditionally known both as the sample handling system and as the carrier pre-heat system.

Referring to FIG. 2A, gas chromatograph 100 includes valve assembly 210 connected to multiple columns 220 and detectors 230, in this case, thermal conductivity detectors (TCD's). A gas sample generally follows path 240 through valve assembly 210, columns 220 and TCD's 230. The valve assembly allows the selection of columns 220 which contain a liquid phase, or porous polymer, or other material. Two types of columns are packed columns and capillary columns. Referring now to FIGS. 2B and 2C, packed columns 220 are filled with a liquid coated solid support or porous polymer. Capillary columns 220 are coated on their interior with a liquid or porous polymer. In either case, the polymer on the inside of the column acts to separate the gas sample into multiple fractions, each fraction that is to be analyzed being sequentially directed to the TCDs (or other detectors) 230. For example, a gas sample may contain various molecular weight hydrocarbon components such as ethane, methane, and heavier molecules. Ideally, each of these components would be analyzed individually. The resulting analysis could be normalized to minimize the effects of varying sample size from one injection to the next. In general, column 220 separates the gas sample so that more volatile components would elute from the column first, followed by less volatile components (although the use of valve switching may cause the components not to elute at the detector in that order).

Referring to FIGS. 3A and 3B, the operation of a sample valve is shown. Valve 300 includes a plurality of valve ports, labeled 1–6. Incoming line 310 provides a gas sample to valve 300. Exhaust line 320 expels the gas sample from the valve 300. Solid lines 330 show open passages between ports, whereas dotted lines 340 indicate blocked passages between the ports.

A solenoid (not shown) places valve 300 into either an ON position, as shown in FIG. 3A, or an OFF position, as shown in FIG. 3B. When a valve is in the ON position, sample gas flows from incoming line 310, through port 1 to port 6, through line 315 and finally through port 3 to port 2 and out exhaust line 320. When the valve is in the OFF position, sample gas flows from incoming line 310, through port 1 to port 2 and out through exhaust line 320. At the same time, carrier gas flows through port 5 to port 6 into line 315 where it displaces the sample gas. The carrier gas then flows from port 3 to port 4 and injects the sample onto the column. Of course, the designation of OFF versus ON is somewhat arbitrary and the opposite nomenclature could also be used.

FIG. 3C illustrates how a pair of valves may operate either alone or in combination with additional valves (not shown). A first valve 300 includes an array of six valve ports. A second valve 350 also includes an array of six valve ports. Associated tubing 310, 315, 320, 325 and 390, and columns 360 and 370 are also shown as well as dual TCD's 380.

Incoming line 310 is attached to a sample transport line (not shown). When first valve 300 is in an OFF position, gas sample flows from incoming line 310 to port 1 to port 2 of the valve 300 and out exhaust line 320. When valve 300 is in an ON position, however, gas sample flows from port 1 to port 6 and then through sample loop 315. That gas then flows from port 3 to port 2 of valve 300 and is expelled out exhaust line 320. At this time, the sample loop 315 is filled with a gas sample. This means that, if valve 300 is turned OFF at this time, a gas sample is trapped within the sample loop 315.

Turning now to valve 350, when it is in an OFF configuration, carrier gas flows from carrier gas input line 390 through port 2 of valve 350, to port 1 and then through carrier tubing 325. At this time, valve 300 is also in an OFF configuration, so that the carrier gas in tubing 325 is forced through port 5 to port 6 and through gas sample tubing 315. Consequently, this action forces the gas sample down column 360 via ports 3 and 4. The gas sample can then additionally be forced through column 370 and into the dual TCD 380 via ports 4 and 3. Thus, the valves may be connected in series to form "channels." Each channel feeds into a corresponding thermistor pair (a measurement thermistor and a reference thermistor), which measures the amount of a component in the process sample. Alternatively, downstream analyzer valves can be arranged in the system to select a desired column or detector. The graph on which the data are presented has a series of peaks corresponding to the detected components (such as ethane, methane, etc.), and is generally referred to as a chromatogram.

FIG. 4 illustrates a simplified gas chromatograph 400 as is broadly known in the art. Sample valve 410 connects to sample-in line 420, sample out line 430, carrier-in line 440 and column line 450. Sample-in line 420 connects to sample shut-off valve 470 upstream of the sample valve 410. Immediately upstream of sample shut off, sample in line 420 connects to a sample pre-heat coil. Further upstream, sample-in line 420 connects to, e.g., a process pipeline (not shown). Downstream of the sample valve 410, column line 450 connects to column 460. Column 460, in turn, connects downstream to the remainder of the gas chromatograph, including TCD 480, with measurement line 481 and reference line 482.

During operation, a sample of fluid is delivered from a process pipeline or similar source through sample-in line 420. Once the sample is inside the sample valve 410, sample shut off valve 470 is actuated, closing off sample valve 410 from the upstream sample source. At this time, the sample in the sample valve 410 is allowed to equilibrate with atmospheric pressure by exhausting or bleeding the excess sample through sample out line 430. The sample valve 410 then actuates, changing the internal flow of the sample valve 410. Carrier-in line 440, holding pressurized carrier gas, such as helium, hydrogen, nitrogen or argon, is now in communication with the sample trapped in the sample valve 410. This carrier gas displaces the sample out column line 450 and to column 460.

In process chromatography, temperature control is one of the most important characteristics of analytical performance. For example, column temperature has a dramatic effect on the retention time of the sample inside the column. As a general rule, a 30° C. decrease in column temperature will double the retention time for a component with a boiling temperature of 227° C. Consequently, each column of a gas chromatograph is heated to an elevated temperature. This may be accomplished by a variety of known devices or techniques. For example, as shown in FIG. 5A, a housing 500 surrounds the column (not shown in FIG. 5A) and includes a fan 510 that forces heated air to the area around the column and warms it. Another method, as shown in FIG. 5B, is to plate the column 520 with gold or other suitable substance and attach electrodes 525 to the ends of the column 520. The column exterior then heats resistively upon electrical stimulation of the electrodes.

In an attempt to improve the analytic response of the columns, an operator my engage in a program of heating and cooling the columns to various temperatures. FIG. 6 illustrates a temperature versus time graph for a "temperature program". As an example, the effect that temperature programming has on component retention times can be illustrated.

By way of explanation, FIG. 7 shows an example of a chromatogram. As various molecules elute from the columns 460 based upon their volatility, they are measured by a concentration-dependent detector such as a thermal conductivity detector (TCD), a flame photometric detector (FPD), a photoionization detector (PID), a helium ionization detector (HID), or an electrolytic detector. The measured values appear on the chromatogram as a series of peaks. The peak maximum corresponds to the absolute retention time (i.e. time elapsed from injection of sample) for each component in the gas chromatograph system, with the area under each peak being related to the concentration of that component in the sample. To operate the system efficiently, the valve switching directs the samples from column to column at predetermined times. The columns are sized to provide adequate time between critical components (i.e. for valve switches).

In laboratory applications, temperature programming is used to shorten the analysis times of heavier samples while improving detection limits through the reduction of "band spreading". Band spreading is the phenomenon where a component curve on a chromatogram becomes spread out and less distinct. FIG. 9 (not to scale) shows the effects of band spreading on a simplified chromatogram.

In FIG. 9, curve 901 is a chromatogram without band spreading, while curve 902 is the corresponding curve with band spreading. The term t represents time, $t_r$ is retention time, h is height, $W_b$ indicates the width at the base of the curve, $W_{0.5}$ represents the width of the curve at half-height, $W_i$ is the width of the curve at the inflection point, and 0.607 h shows the height of the curve at the inflection point. With band spreading, it is more difficult to identify these points accurately. Further, if the band curve becomes spread beyond the desired switching time, a portion of the curve would not be measured by the chromatograph. Alternately, the valve switching time could be delayed for the elution of the component but this would lead to longer analysis times. It is important to have short analysis times in process chromatography to provide good process control. Thus, excessive band spreading results in measurement errors or longer analysis times.

With a linear temperature program rate, the spacing between members of a homologous series is linear rather than logarithmic and the peak widths are nearly constant. For example, FIG. 8A shows a gas chromatogram for an isothermal (i.e. constant temperature) column. FIG. 8B illustrates the same gas sample analyzed with a temperature programmed column.

One problem with temperature programming is that there exists a time lag between heating the exterior of the column and the heating of the interior of the column (where the sample is). Consequently, the program must be adjusted and timed to ensure that the inner portion of the column is at the correct temperature. Another problem with temperature programming is the trade-off between a decrease in analysis time and the cooling time required to achieve the starting temperature. In other words, for process (on-line) applications, the problem is even more complicated, because the laboratory techniques used to shorten the cool-down time such as cryogenic (liquid nitrogen) cooling aren't practical for process (on-line) applications. The vortex chillers used in process chromatographs require high-pressure (>100 psig) instrument air for optimum efficiency. Unfortunately, many field locations don't have high-pressure instrument air available.

In addition, if the temperature program is not highly reproducible, then where two components elute very close in time, their position on the gas chromatogram could be switched. For example, the retention of highly branched isomers could be transposed with only slight variations in temperature. This could result in components being misidentified.

Further, even where the column is fully heated to the correct temperature, of "band spreading" can still result. The problem of band spreading arises in part from the heating of the sample and carrier gas as they move through the column. The sample and carrier gas are at a lower temperature than the column as the sample and carrier gas enter the column. But gradually, the sample and carrier gas are heated by the surrounding column, decompressing and accelerating to a higher velocity. As a result of the decompression of the sample and carrier streams in the column, most of the separation of components in the sample is completed at the front of the column. In a 60-meter capillary column, a majority of the separation might occur in the first few meters of the column.

Historically, chromatograph research has focused on developing small diameter capillary columns to compensate for this problem. However, this solution has been unsatisfactory because the complexity of the gas chromatograph varies directly with column diameter and the reliability varies inversely. Thus, gas chromatographs with very small column diameter (i.e. <0.25 mm inner diameter) are impractical for process (on-line) applications.

Another contribution to band spreading is the kinetic rate of transfer of sample molecules between the mobile (carrier gas) and stationary (liquid) phases. The equilibrium between the two phases is established so slowly that the column always operates under nonequilibrium conditions. Since the diffusion coefficient varies inversely with temperature (i.e. the column efficiency varies directly with temperature), the component retention time shifts earlier when the temperature is increased. Likewise, the retention time shifts later when the temperature is decreased.

Other problems with the arrangement of FIG. 4 also exist. Another problem is "retention time drift" that arises from fluctuations in temperature of the carrier gas. Thus, where there is retention time drift, the entire curve might shift to the right or the left. This is a problem because where the component peaks overlap or extend beyond the switching time for a corresponding analyzer valve, the offending portion of the curve is not measured by the chromatograph.

In process chromatography, it is important to have short analysis times to provide sufficient analytical feedback for process control. For this reason, the process chromatographer sets the switching times as close together as realistically possible to provide the fastest possible chromatograph, and so merely allowing more component separation (i.e. longer analysis times) is not a best-case solution.

It has been believed to be desirable, therefore, to control the inlet carrier gas at a temperature optimized for the gas chromatograph temperature, usually chosen in the range of 80–85° C. with little variation. It has been difficult to heat the inlet gas to a consistent temperature, however. One effort involved placing a length of tubing inside a heated zone, while at the same time, coiling the tubing in a compressed corkscrew manner to conserve space. However, even heating of very long coils of tubing, such as 50-foot coils, does not reliably heat the inlet gas to the desired temperature. This is due to the fact that the ambient temperature of a process gas chromatograph varies from −18 to 55° C. For this reason, the resulting temperature of the inlet gas should be monitored using a Platinum resistance thermal detector (RTD) inserted into the gas stream.

A related problem is variation in component retention time arising from fluctuations in the inlet carrier pressure. Since inlet pressure fluctuations affect the carrier flow rate, they also result in retention time drift. It is desirable therefore to eliminate or minimize these variations in inlet carrier pressure.

As can be seen, a number of problems exist with current gas chromatographs and a gas chromatograph is needed that solves these and other problems. The ideal process gas chromatograph would be both fast and accurate, eliminating or severely reducing many of the measurement errors known in the prior art. It would also be simple and inexpensive to manufacture. In a perfect world, the device or method that solves these problems would do so on its own, requiring little human supervision or maintenance. It would also have considerable longevity, including being sturdy and not prone to breakage.

SUMMARY OF THE INVENTION

One embodiment of the invention is a gas chromatograph including a column to separate components of a fluid sample, a valve switch connected upstream of the column and downstream of sample and carrier gas sources, and first and second heaters for heating the column and carrier gas stream, respectively. The carrier gas stream is heated to one or more temperatures higher than the temperature of the column.

BRIEF DESCRIPTION OF THE DRAWINGS

For a more detailed description of the preferred embodiment of the present invention, reference will now be made to the accompanying drawings, wherein:

FIG. 2C is a cut-away view of a capillary column;

FIG. 3C is a schematic diagram of a multiple valve system for analyzing a sample;

FIG. 7 is a chromatogram from a gas chromatograph;

DETAILED DESCRIPTION

Embodiments of the invention ameliorate the problems discussed above. Examination of the mathematics-underlying column and chromatograph efficiency illustrates principles used by the invention to achieve a more accurate chromatograph.

From the Van Deemter Equation for packed columns, it is known that:

$$h = 2\lambda d_p + 2\gamma D_{g,T} fj/u + \omega d_p^2 fu/D_{g,T} j + 2k d_f^2 u/[3(1+k)^2 D_{1,t}] \qquad (1)$$

with these variables defined as explained below.
In other words, equation (1) may be restated as:

$h$=eddy diffusion+longitudinal diffusion+resistance to mass transfer in the mobile phase+resistance to mass transfer in the stationary phase.

From the Golay-Gidding Equation for capillary columns, it is known that:

$$h = 2D_{g,T} fj/u + (11k^2 + 6k + 1) r_c^2 fu/[24(1+k)^2 D_{g,T}] j + 2k d_f^2 u/[3(1+k)^2 D_{1,t}] + \sigma^2 u^2/(1+k)^2 L \qquad (2)$$

In other words, equation (2) may be restated as:

h=longitudinal diffusion+resistance to mass transfer in the mobile phase+resistance to mass transfer in the stationary phase+extra column effects.

where,
- h=column efficiency defined as height equivalent to a theoretical plate
- λ=approximately 0.5, distribution factor
- $d_p$=particle diameter
- γ=approximately 0.7, obstructive factor due to the tortuous path taken by the solute molecule
- $D_{g,T}$=diffusion coefficient of the solute molecule in the gas phase (function of temperature)
- f=(9/8)[$(P^4-1)(P^2-1)/(P^3-1)$], Gidding plate height correction (gas expansion) factor, where
- P=$p_i/p_o$, where
    - $p_i$=inlet pressure, and
    - $p_o$=outlet pressure
- j=(3/2)$(P^2-1)(P^3-1)$, James Martin compressibility factor, where
    - P=$p_i/p_o$
- u=mobile phase (carrier gas) linear velocity
- ω=approximately 0.002 to 5, packing factor to correct for radial diffusion
- k=capacity factor (partition ratio) of the solute
- $d_f$=film thickness of the stationary phase
- $D_{1,T}$=diffusion coefficient of the solute in the stationary phase (function of temperature)
- $r_c$=diameter of column
- σ=variance due to extra column effects
- L=length of column It can be seen from these equations that column efficiency is increased as longitudinal diffusion is minimized. This depends on the diffusion coefficient, $D_{g,T}$, being minimized. Consequently, careful analysis reveals that the prior art technique of heating the column to a higher temperature than the sample and carrier gas stream does not maximize column efficiency.

As explained above, where the sample warms as it proceeds down the column, it expands. This expansion results in band spreading. If, instead (and according one aspect of the invention), the sample and carrier gas are heated to a temperature above that of the column, the sample tends to contract as it moves down the column, decreasing the diffusion coefficient. This contraction also results in "band focusing" on the chromatogram, the opposite of band spreading.

Figure 1:
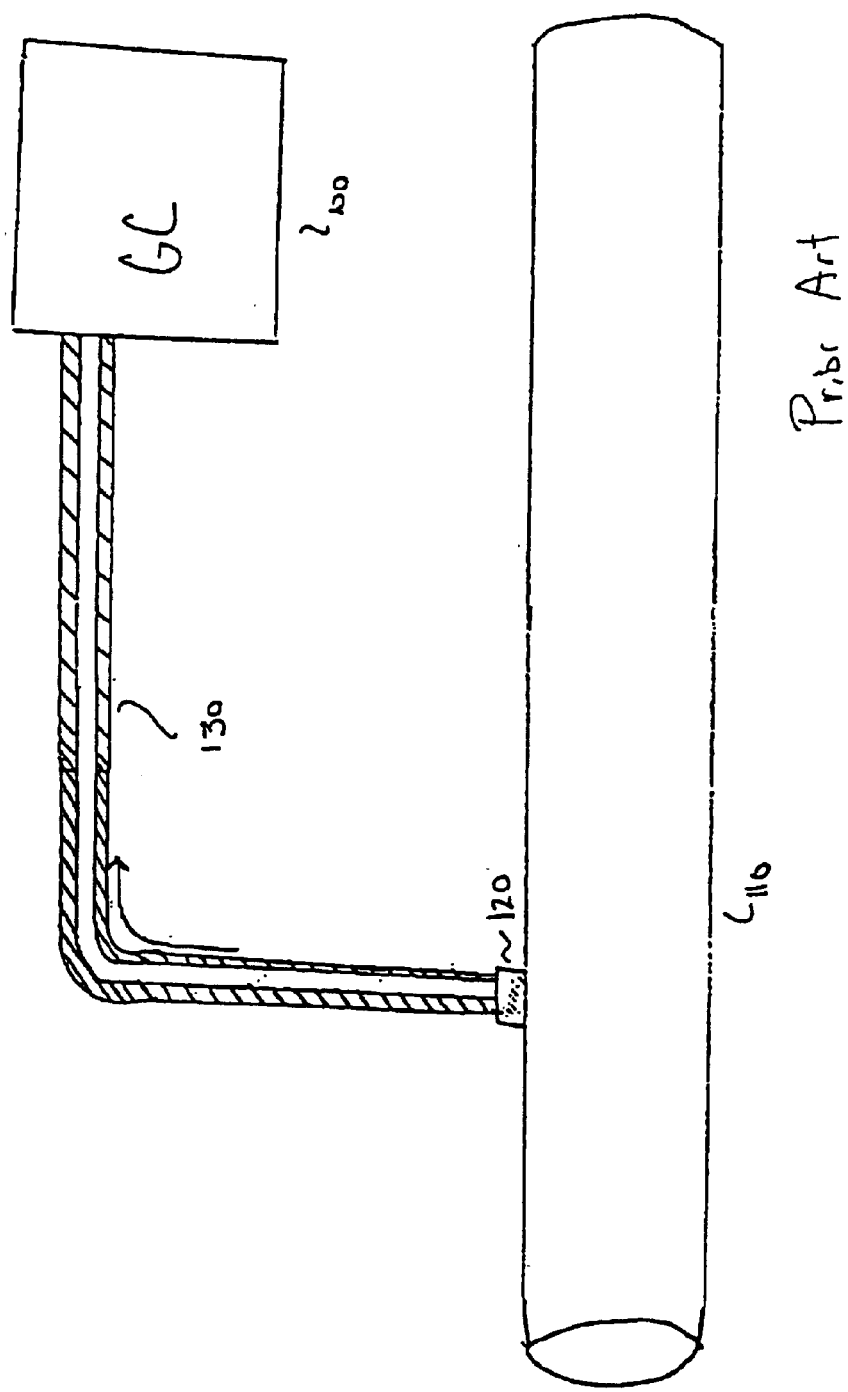
FIG. 1 is a simplified diagram of a gas chromatograph system.
Figure 2A:
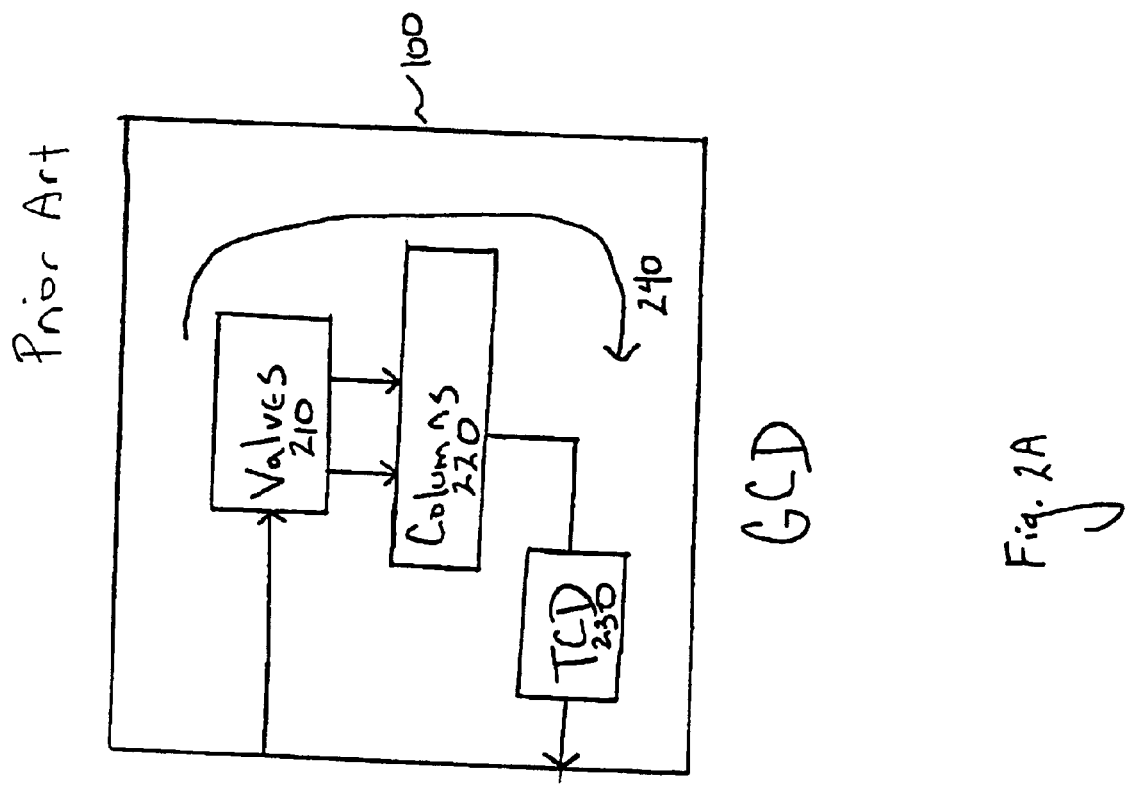
FIG. 2A is a simplified schematic of a gas chromatograph.
Figure 2B:
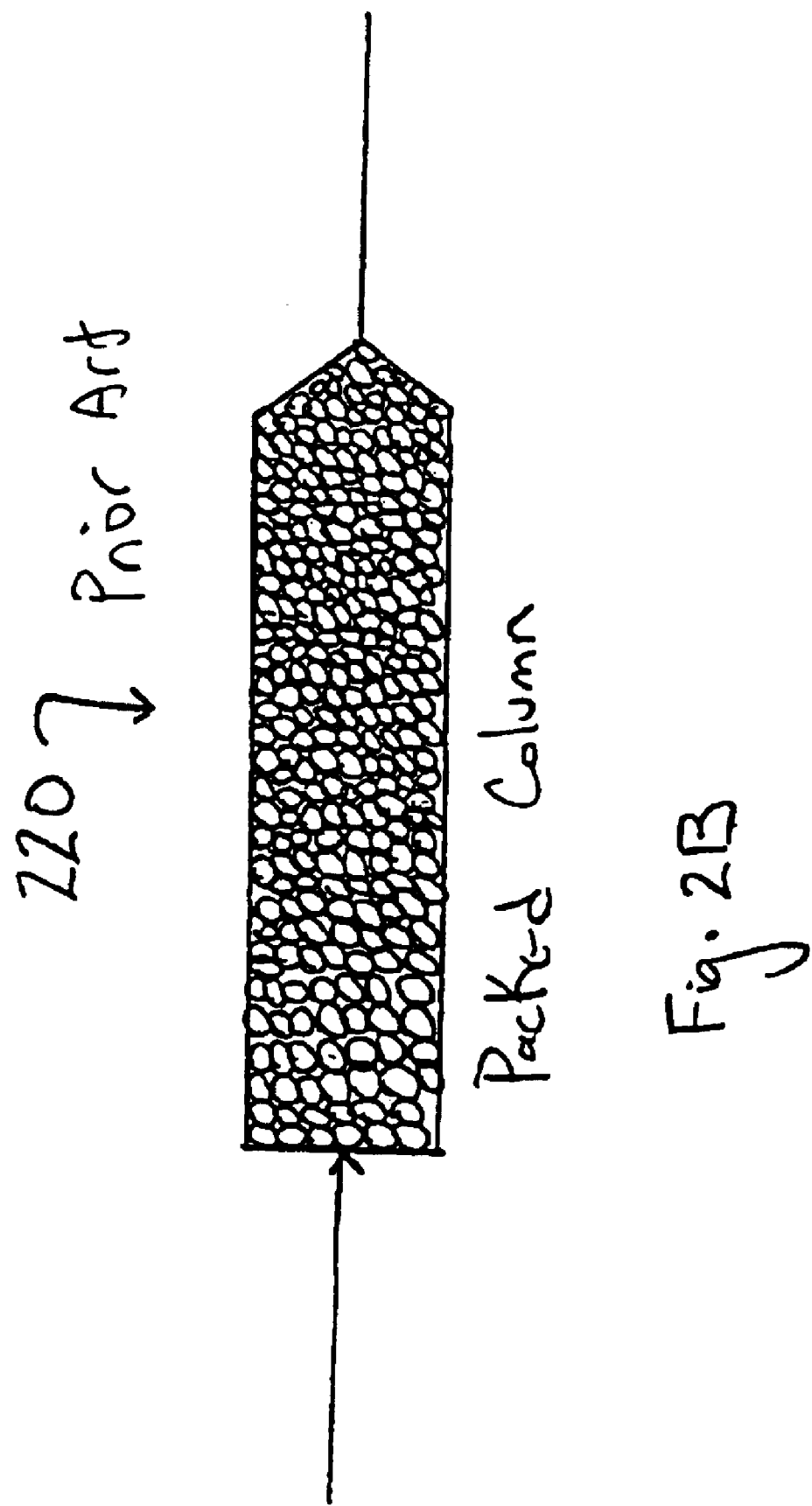
FIG. 2B is a cut-away view of a packed column.
Figure 3B:
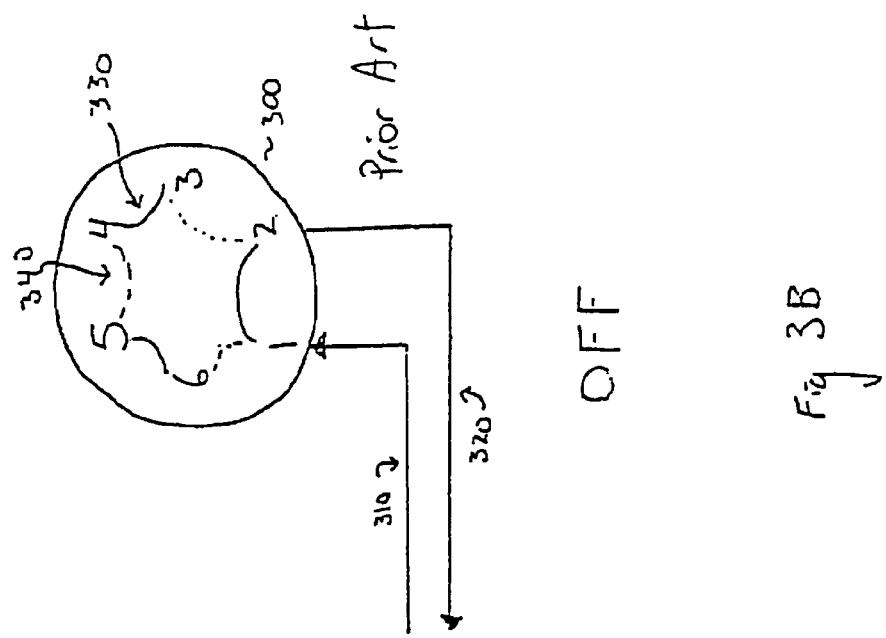
FIG. 3B is a schematic diagram of a valve in an ON configuration.
Figure 3A:
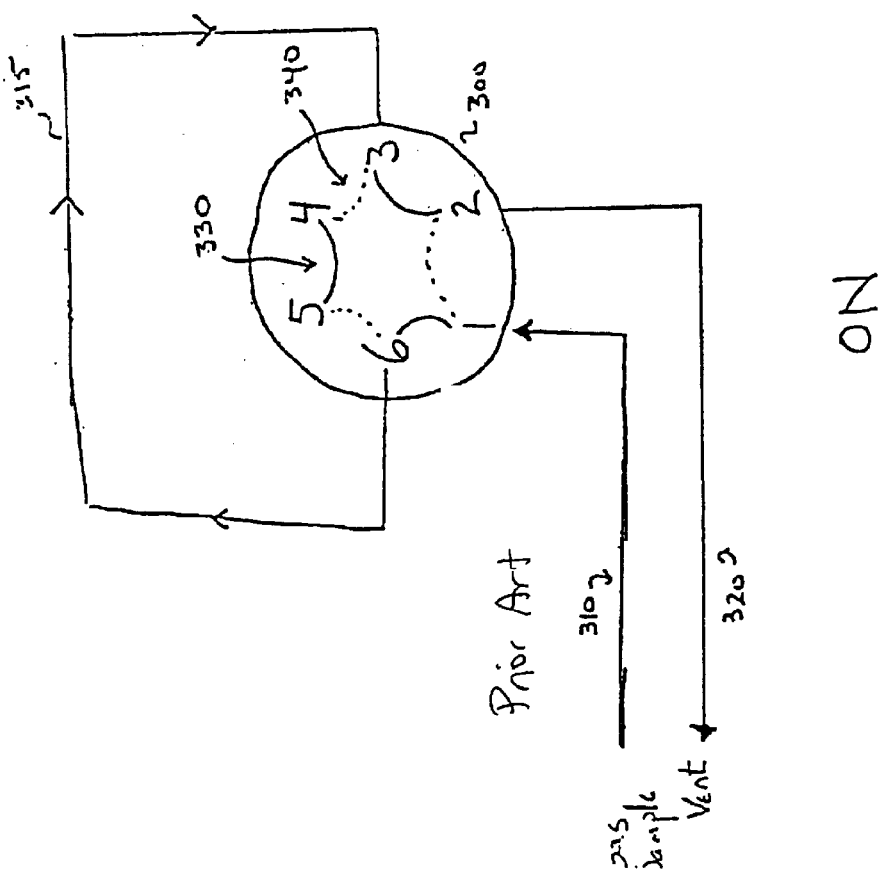
FIG. 3A is a schematic diagram of a valve in an OFF configuration.
Figure 4:
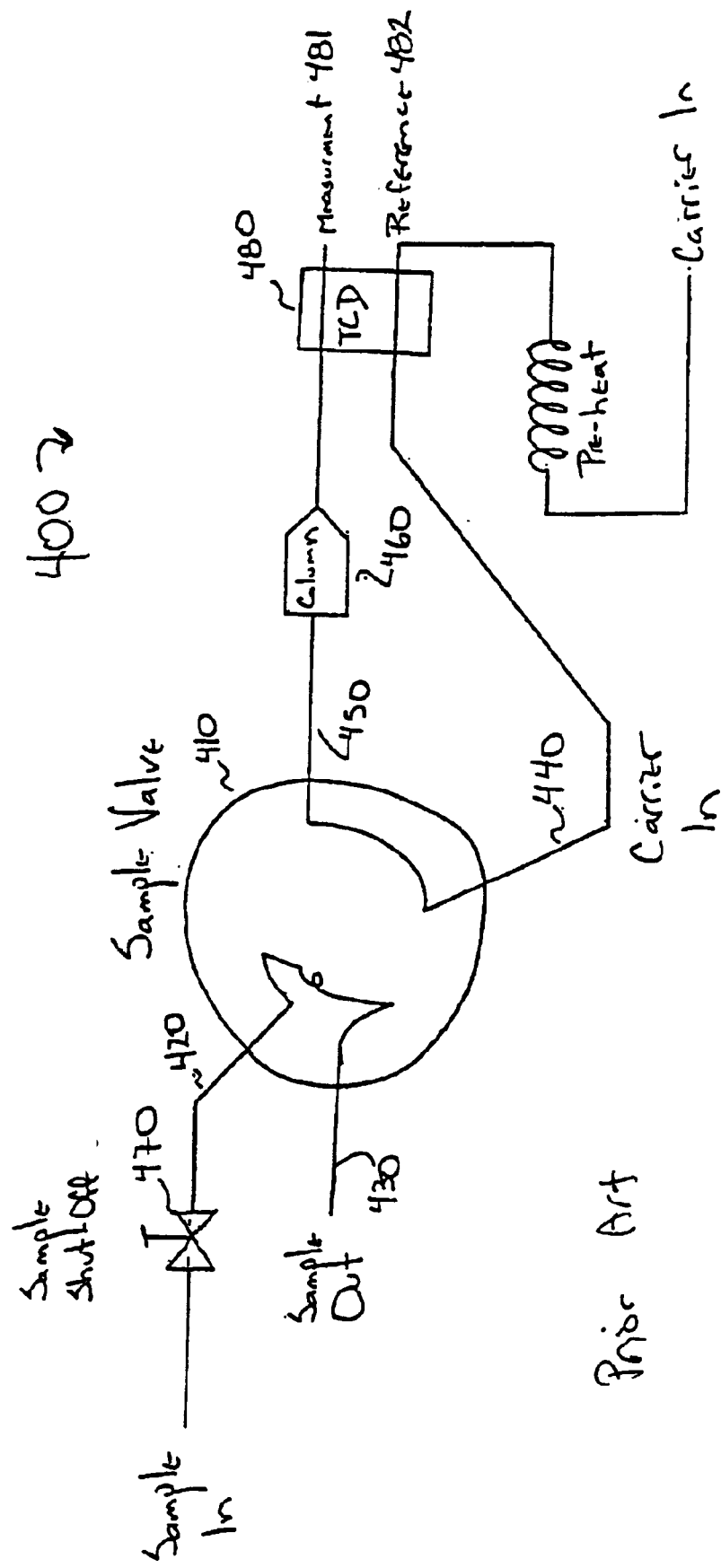
FIG. 4 is a schematic diagram of a simple gas chromatograph.
Figure 5A:
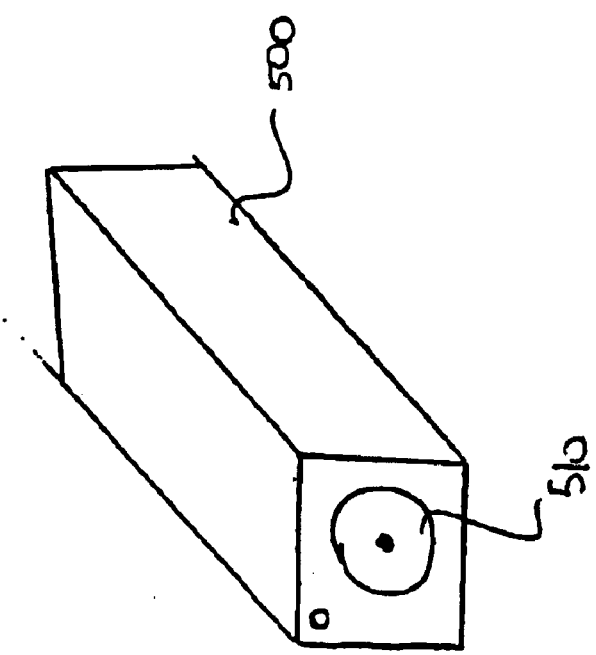
FIG. 5A is a perspective view of a fan housing surrounding a column.
Figure 5B:
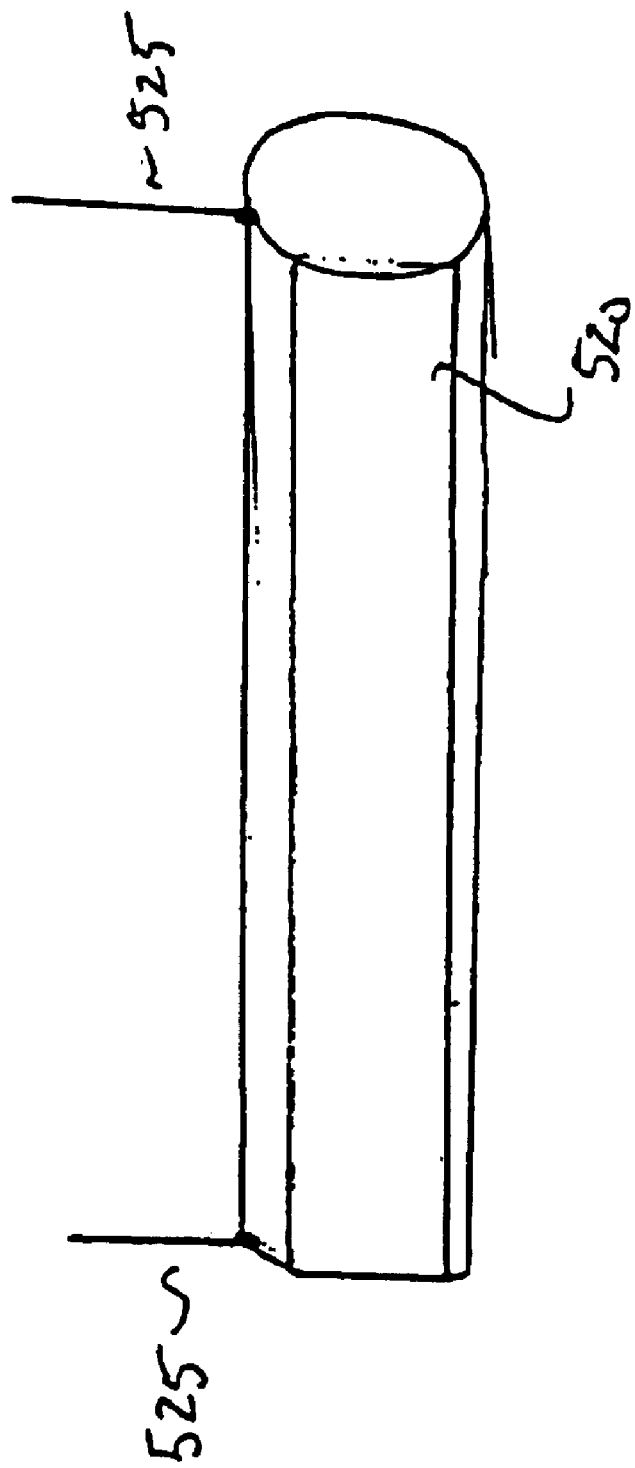
FIG. 5B is a perspective view of a plated column heated by electrodes.
Figure 6:
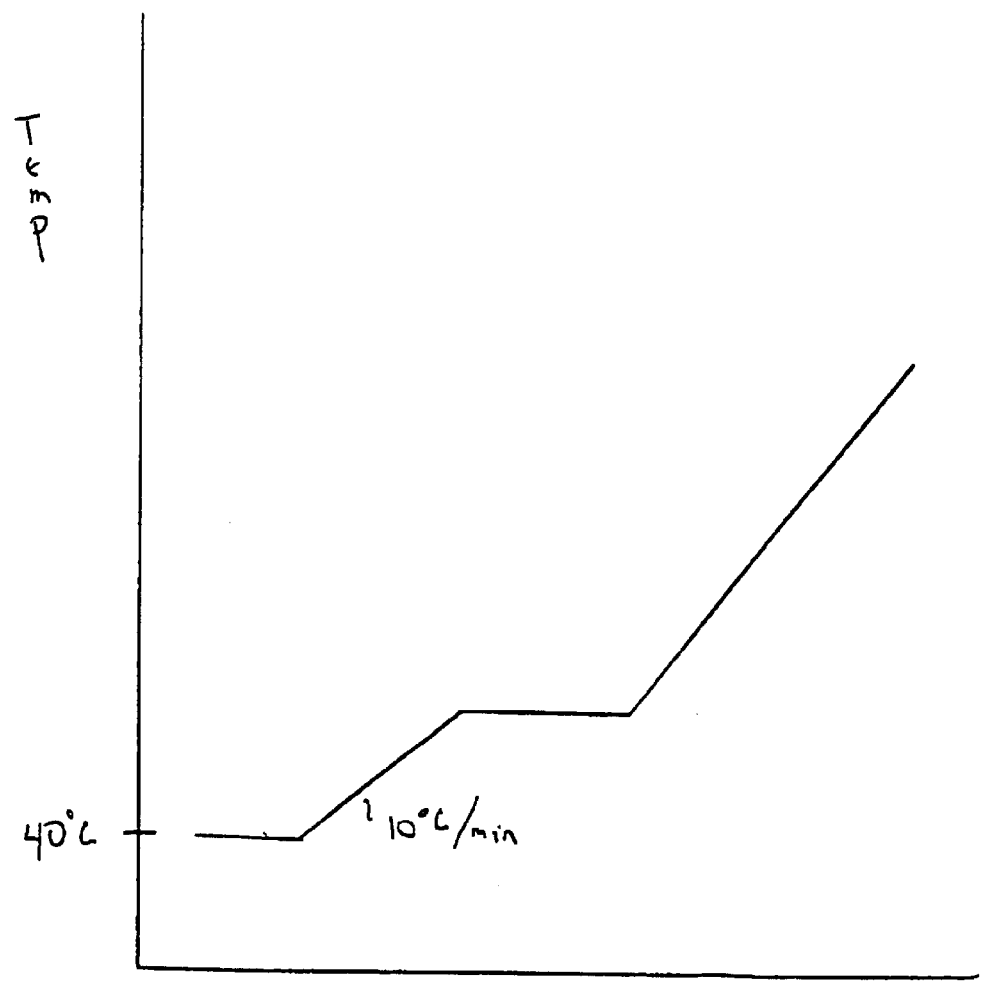
FIG. 6 is a graph of a temperature program.
Figure 8A:
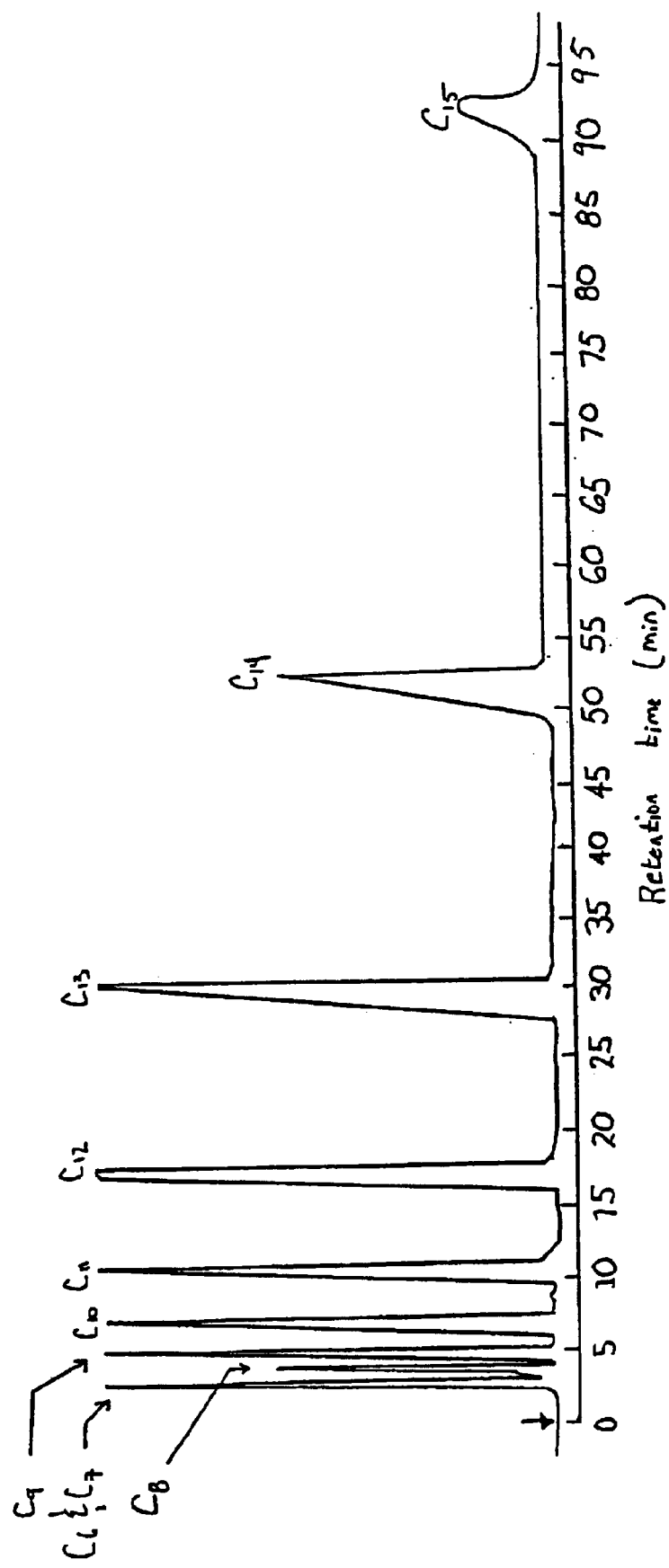
FIG. 8A is a gas chromatogram of a sample without using temperature programming.
Figure 8B:
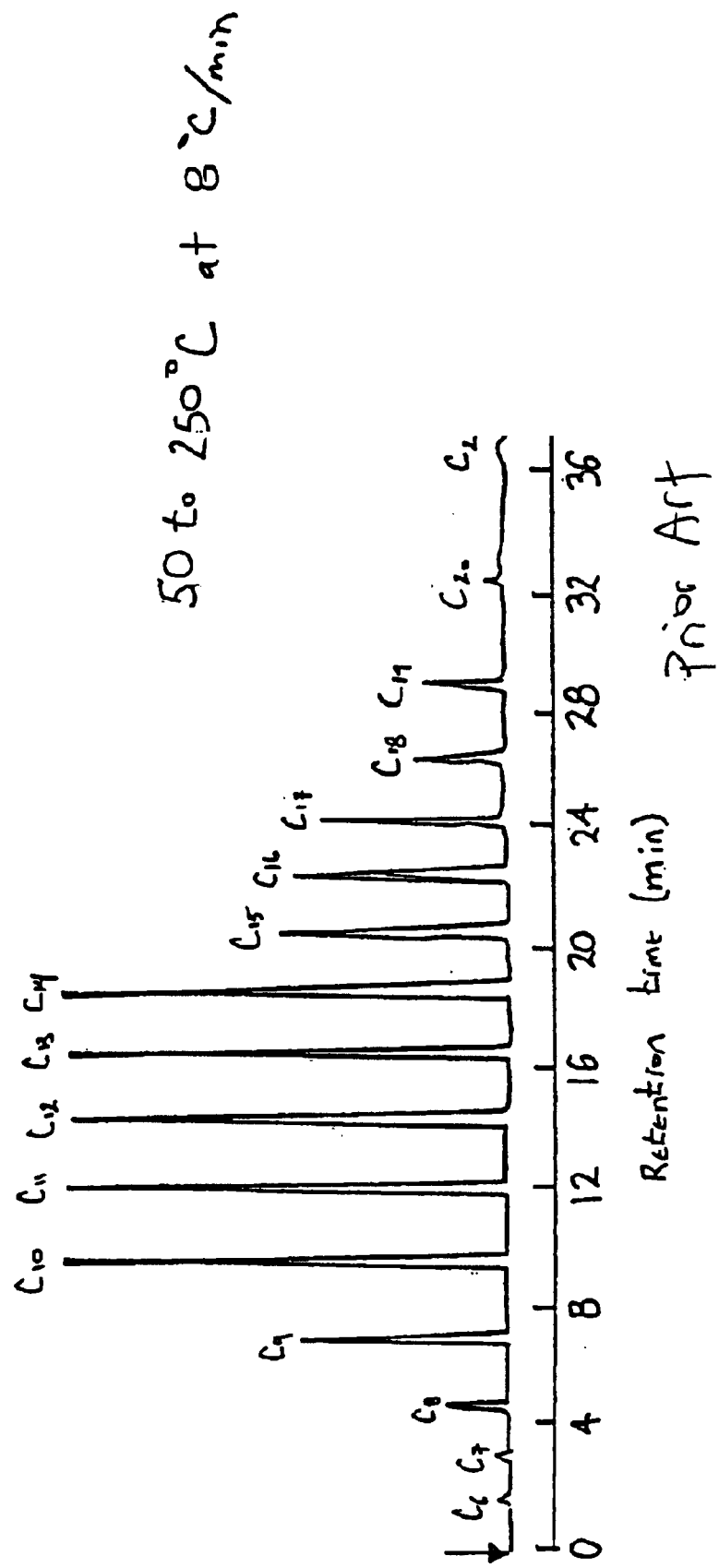
FIG. 8B is a gas chromatogram of a sample with using temperature programming.
Figure 9:
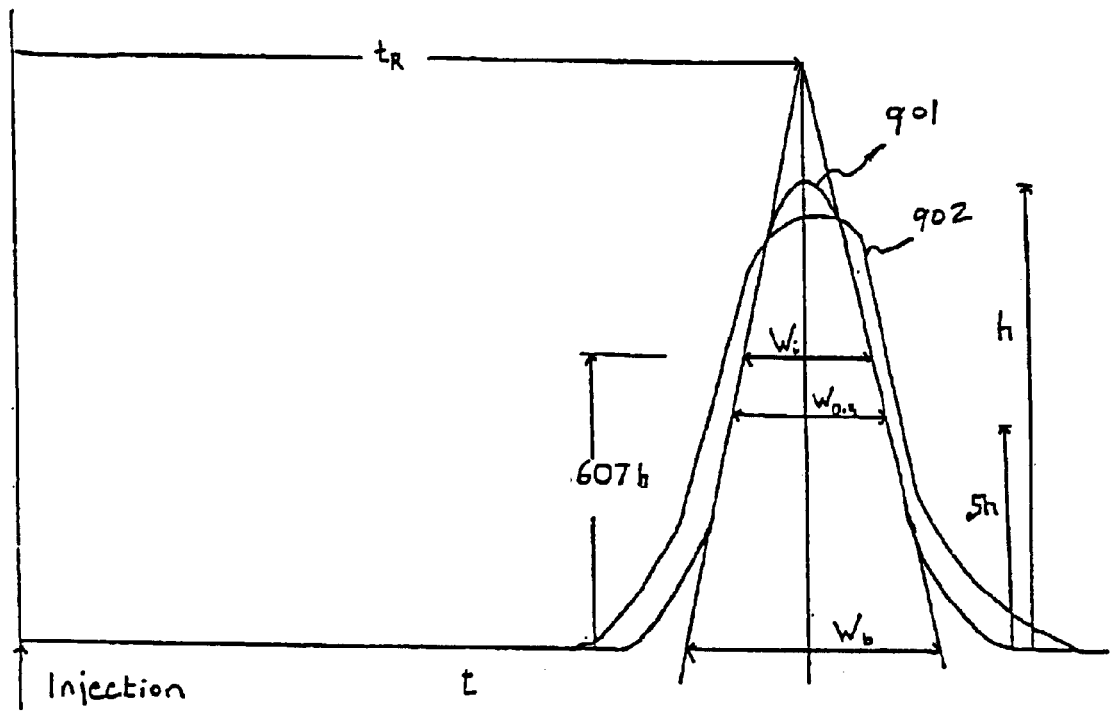
FIG. 9 is a simplified chromatogram showing band spreading.
Figure 10:
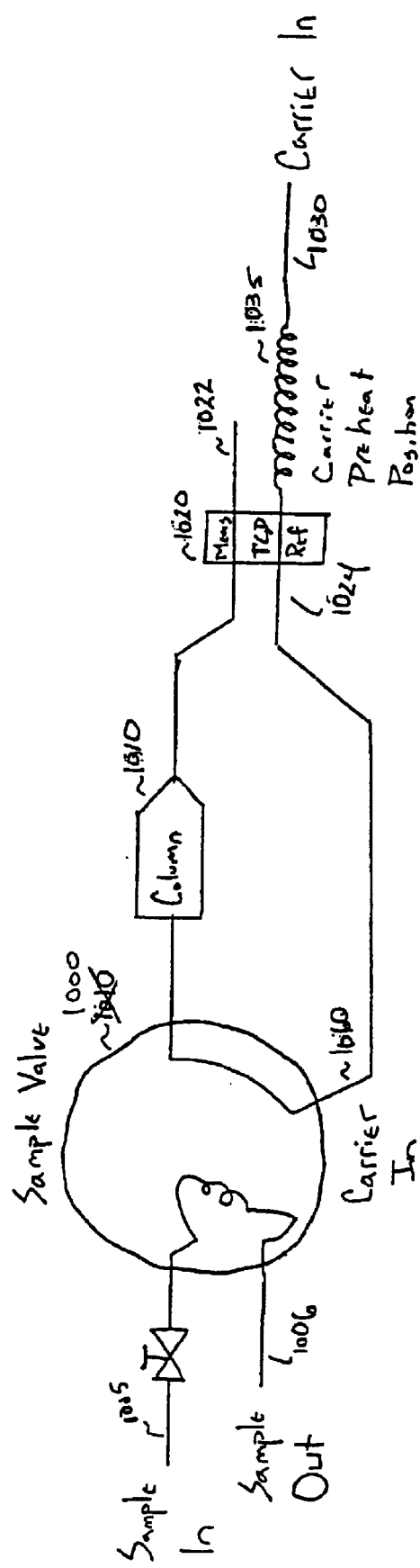
FIG. 10 is a schematic of a first embodiment of the invention.

FIG. 10 shows a first embodiment of the invention for an isothermal application. A sample valve 1000 attaches to sample-in line 1005 and sample exhaust line 1006. Sample valve 1000 also attaches to carrier-in line 1060 on an upstream side, and column 1010 on a downstream side. Column 1010 attaches to the measurement line 1022 of TCD 1020. First carrier-in line 1030 is coiled along its length, resulting in a carrier pre-heat location 1035 in a temperature oven. Downstream of carrier pre-heat 1035 is the reference line 1024 of TCD 1020, which connects to sample valve 1000 via carrier-in line 1060. According to a first aspect of this invention, the carrier gas stream should be heated to a higher temperature than the column. In particular, the carrier gas stream should be heated to about 5–10 degrees Celsius higher than the column temperature. Where the column is maintained at a constant temperature of 70° C., the carrier gas may be in the range of 75 to 80 degrees.

The principle of heating the carrier stream to a higher temperature than the column may also be used in conjunction with a temperature program. From the temperature-programmed equation developed by Jian Ying Zhang, it is known that $$h = \frac{L}{t^2} \int_0^L \frac{h_z}{R_t^2 v_{t,z}^2} dz \quad (3)$$

where
- h=column efficiency defined as height equivalent to a theoretical plate
- L=length of column
- t=time
- $h_z$=A+Bj$D_{g,T}/v_{t,z}$+Cv/j$D_{g,T}$+D$v_{t,z}$, where
    - $h_z$=local column efficiency;
    - $D_{g,T}$=diffusion coefficient of the solute molecule in the gas phase (function of temperature); and
    - A,B,C and D=coefficients
- $R_t$=ratio of zone velocity to carrier gas velocity (function of time)
- $v_{t,z}$=mobile phase (carrier gas) local velocity (function of time and position)
- z=position of component zone (band) center The maximum column efficiency is obtained when h is minimized. Once again, it can be seen that column efficiency varies directly with the diffusion coefficient, $D_{g,T}$.

Figure 11:
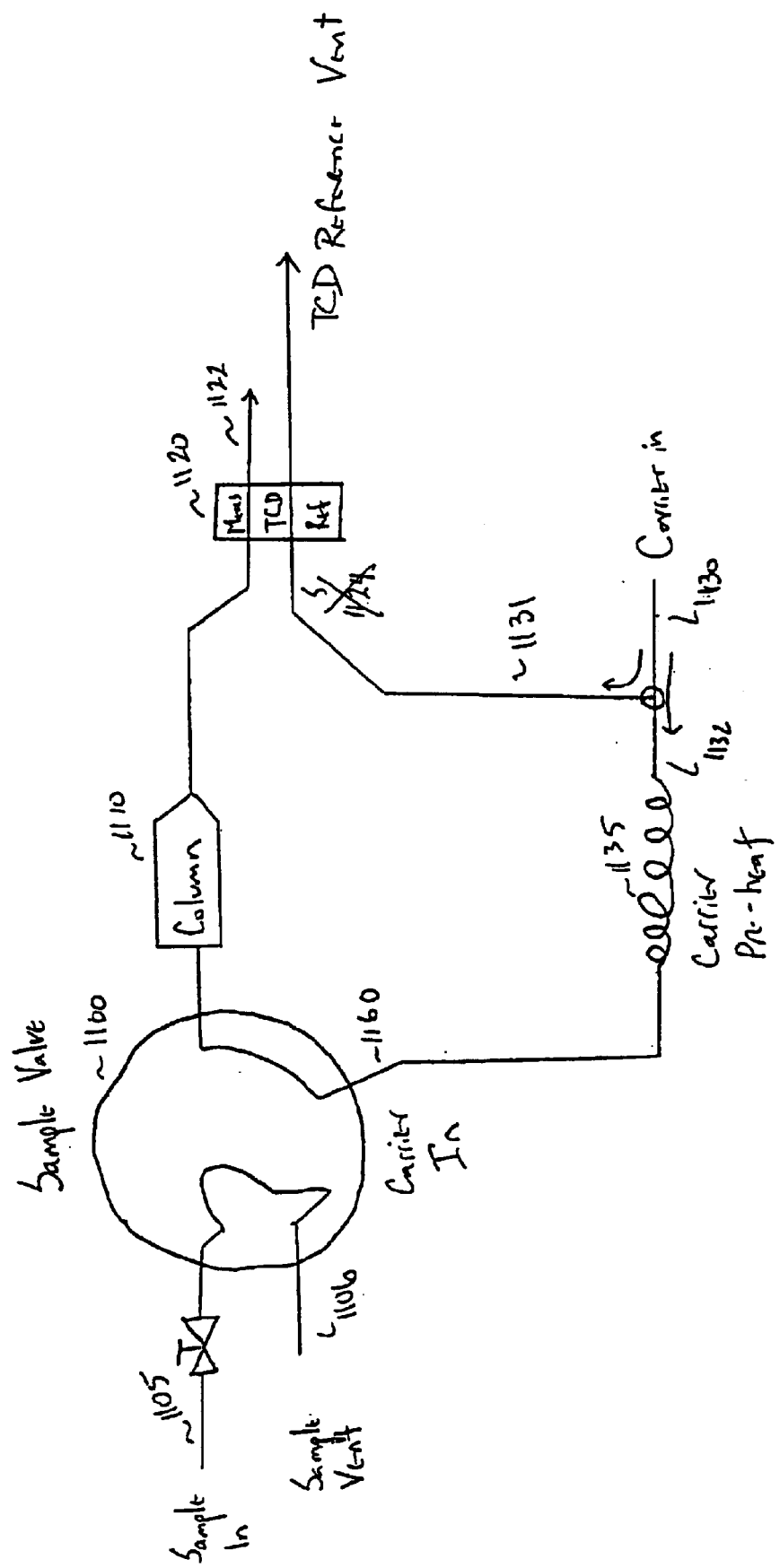
FIG. 11 is a schematic of a second embodiment of the invention.

FIG. 11 shows a second embodiment of the invention for a temperature programmed application. A sample valve 1100 attaches to sample-in line 1105 and sample exhaust line 1106. Sample valve 1100 also attaches to carrier-in line 1160 on an upstream side, and column 1110 on a downstream side. Column 1110 attaches to the measurement line 1122 of TCD 1120. First carrier-in line 1130 splits into two carrier streams. First carrier tubing 1131 serves as the reference line for the TCD 1120. Second carrier tubing 1132 coils along its length, resulting in a carrier pre-heat location 1035 in a temperature oven. Downstream of carrier pre-heat location 1135 is the carrier-in line 1160.

Figure 12:
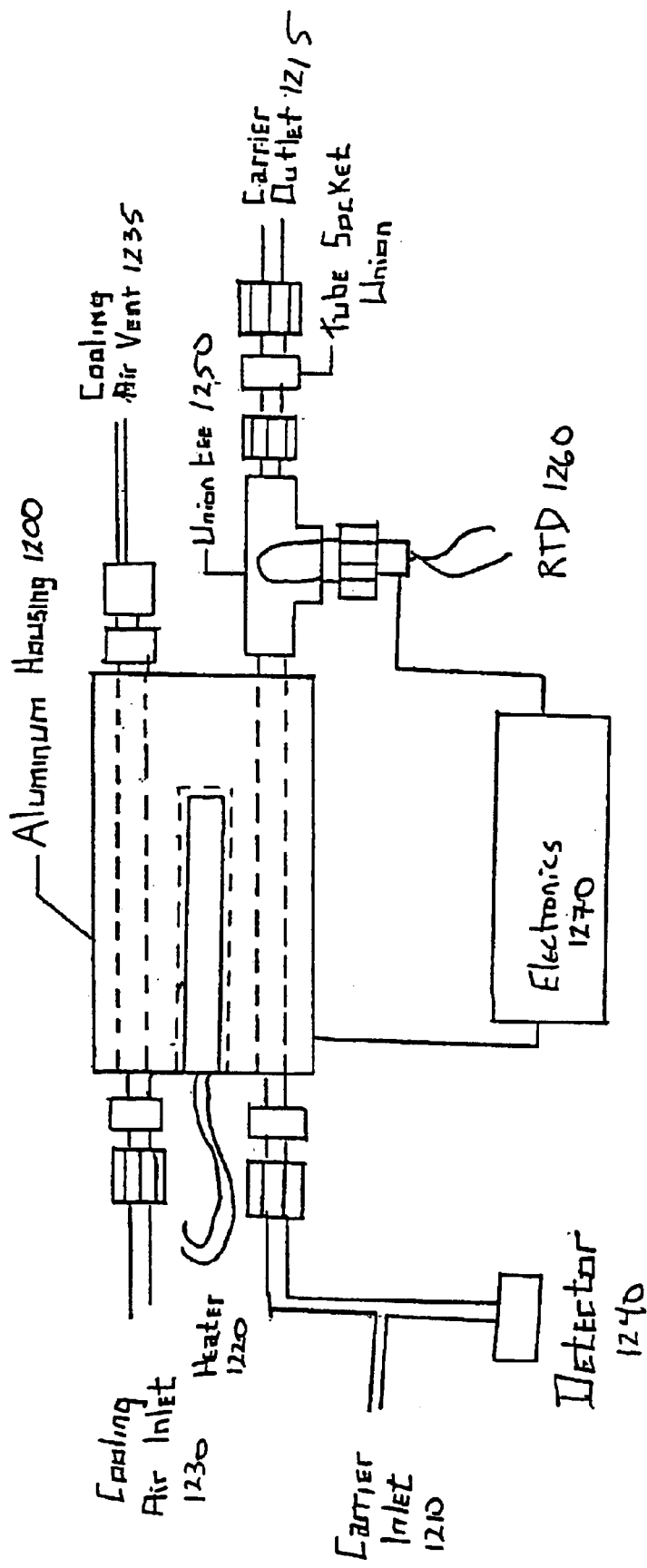
FIG. 12 is an improved carrier preheat system for temperature program applications.

FIG. 12 illustrates an improved carrier preheat system particularly suited for temperature program applications. An aluminum housing 1200 connects to a carrier gas inlet 1210 and carrier gas outlet 1215. Aluminum housing 1200 encases a heater 1220 to heat the carrier gas traveling though the housing, and connects to a cooling air inlet 1230 and cooling air vent 1235 that cool the carrier gas traveling through the housing 1200. A detector 1240 measures the temperature of the carrier gas as it enters the housing. A union tee 1250 with attached temperature detector RTD 1260 measures the temperature of the carrier gas as it leaves the housing. Electronics 1270 connect to the RTD and the heater 1220 and adjust the temperature of the carrier gas to achieve the temperature program.

Further, although FIG. 12 shows a device to heat and warm a single carrier gas stream to various temperatures, it would also be possible to switch among multiple carrier gas streams, maintained at different temperatures, to accomplish the temperature variations used for temperature programming.

A second aspect of the invention that can be advantageously used in combination with the first aspect of the invention is the use of a backpressure restrictor upstream of the columns, and preferably upstream of the one or more sample valves. The largest contributing factor to h in equation (2), column efficiency, is the resistance to mass transfer in the stationary (liquid) phase of the packed columns (and for capillary columns with heavier film thickness (i.e. >0.25 microns)). Looking at equation (2), there are two variables in the resistance to mass transfer of the stationary phase term (i.e. $2kd_f^2u/[3(1+k)^2D_{1,T}]$) that may be controlled. In particular, the carrier gas rate, u, may be controlled. For this type of column, column inefficiency typically varies directly with the mobile phase (carrier gas) velocity and inversely with diffusion of solute in the stationary phase. Since inlet pressure is the driving force behind the carrier velocity, fluctuations in inlet pressure typically lead to variations of component retention times.

In addition, the diffusion coefficient of the solute in the stationary phase, $D_{1,T}$, may be controlled. Since the diffusion coefficient varies inversely with temperature (i.e. the column efficiency varies directly with temperature), changes in temperature also lead to variations of component retention times.

For capillary columns with light film thickness (i.e. <0.25 microns), the resistance to mass transfer in the mobile phase predominates. Looking at equation (3), there are four variables in the resistance to mass transfer in the mobile phase (i.e. $(11k^2+6k+1)r_c^2fu/[24(1+k)^2D_{g,T}]j$) that may be controlled. In particular, the column efficiency, h, is once again directly related to the carrier gas linear velocity, u. Again, since inlet pressure is the driving force behind the carrier linear velocity, fluctuations in inlet pressure typically lead to variations of component retention times.

In addition, in equation (2) and (3) both the gas expansion factor, f, and the compressibility factor, j, are dependent upon P, the ratio of the inlet pressure to the outlet pressure. Using L'Hopitals Rule, the limit of the gas expansion factor as the pressure ratio approaches unity can be calculated as, $$\lim f(P \to 1)=1$$

Similarly, the limit of the compressibility factor can be calculated as, $$\lim j(P \to 1)=1$$

As can be seen from Equation (1) for packed columns, minimizing the pressure ratio will result in minimizing the longitudinal diffusion and resistance to mass transfer in the mobile phase terms. As the pressure ratio approaches unity, $$\lim h(P \to 1)=2\lambda d_p+2\gamma D_{g,T}/u+\omega d_p^2 u/D_{g,T}+2kd_f^2u/[3(1+k)^2 D_{1,T}] \quad (4)$$

In other words, as the column inlet pressure approaches the column outlet pressure, an improvement is made in column efficiency because of improvements in longitudinal diffusion and resistance to mass transfer in the mobile phase. However, because resistance to mass transfer in the stationary phase usually predominates in packed columns, the improvement in column efficiency for packed columns by achieving a pressure ratio approaching unity is minimal.

For capillary columns with light film thickness, minimizing the pressure ratio will result in minimizing the longitudinal diffusion and resistance to mass transfer in the mobile phase terms. From Equation (2) for capillary columns, as the pressure ratio approaches unity, $$\lim h(p \to 1)=2D_{g,T}/u+(11k^2+6k+1)r_c^2 u/[24(1+k)^2 D_{g,T}]+2kd_f^2u/[3(1+k)^2 D_{1,T}]+\sigma^2 u^2/(1+k)^2 L \quad (5)$$

Because the resistance to mass transfer in the mobile phase predominates for capillary columns with light film thickness (i.e. <0.25 microns), achieving a pressure ratio approaching unity would significantly improve column efficiency.

The resistance to mass transfer in the stationary phase is due to the kinetic rate of transfer of sample molecules between the mobile (carrier gas) and stationary (liquid) phases. The equilibrium between the two phases is established so slowly that the column always operates under nonequilibrium conditions. Since the diffusion coefficient in the stationary phase, $D_{1,T}$, varies inversely with temperature (i.e. the column efficiency varies directly with temperature), the component retention time shift earlier when the temperature is increased. Likewise, the retention time shifts later when the temperature is decreased.

Thus, although equations (1) and (2) assume a constant gas inlet pressure, it may be inferred that column efficiency varies with, carrier gas flow rate, and inlet pressure. Further, once the cause of the measurement errors is understood, as well how their magnitude is affected by changing variables in the gas chromatograph, it is necessary to formulate a method or structure to maintain a constant and carrier gas flow.

It has been found that although pressure gradient is the driving force behind carrier linear velocity, improved efficiency can be achieved through proper placement and optimization of backpressure restrictors.

Figure 13:
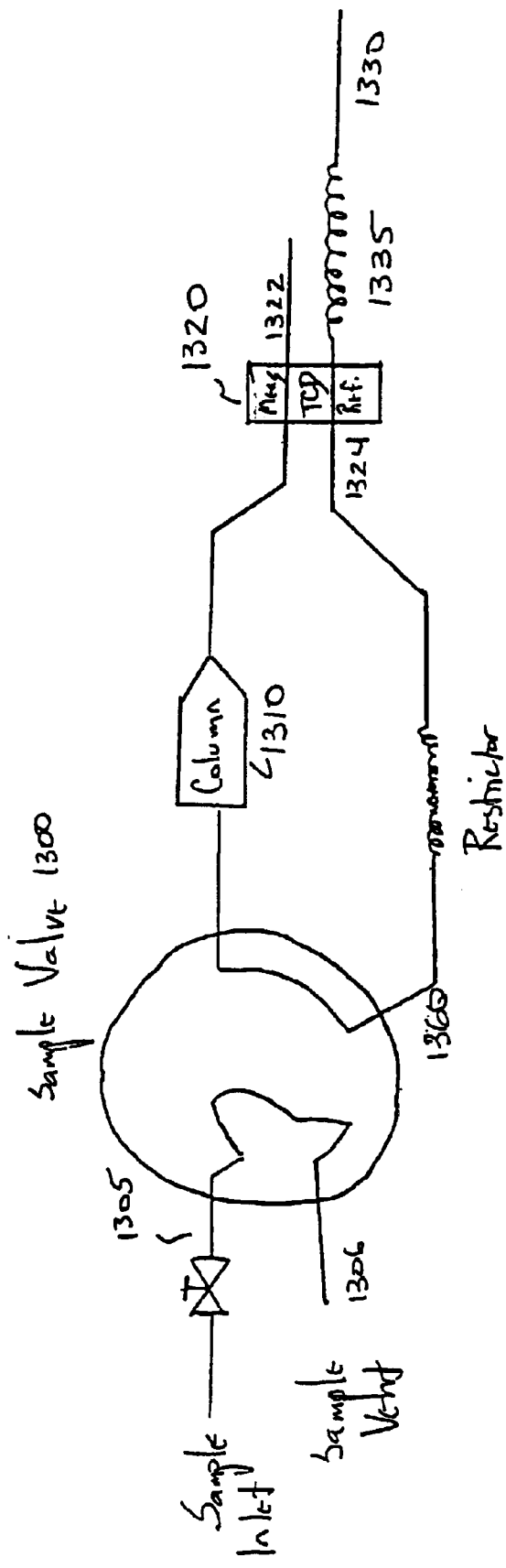
FIG. 13 is a schematic of a third embodiment of the invention.

FIG. 13 is the system of FIG. 10 with the addition of a back pressure restrictor upstream of the column. FIG. 13 shows a first embodiment of the invention for an isothermal application. A sample valve 1300 attaches to sample-in line 1305 and sample exhaust line 1306. Sample valve 1300 also attaches to carrier-in line 1360 on an upstream side, and column 1310 on a downstream side. Column 1310 attaches to the measurement line 1322 of TCD 1320. First carrier-in line 1330 is coiled along its length, resulting in a carrier pre-heat location 1335 in a temperature oven. Downstream of carrier pre-heat 1335 is the reference line 1324 of TCD 1320, which connects to sample valve 1300 via carrier-in line 1360.

Figure 14:
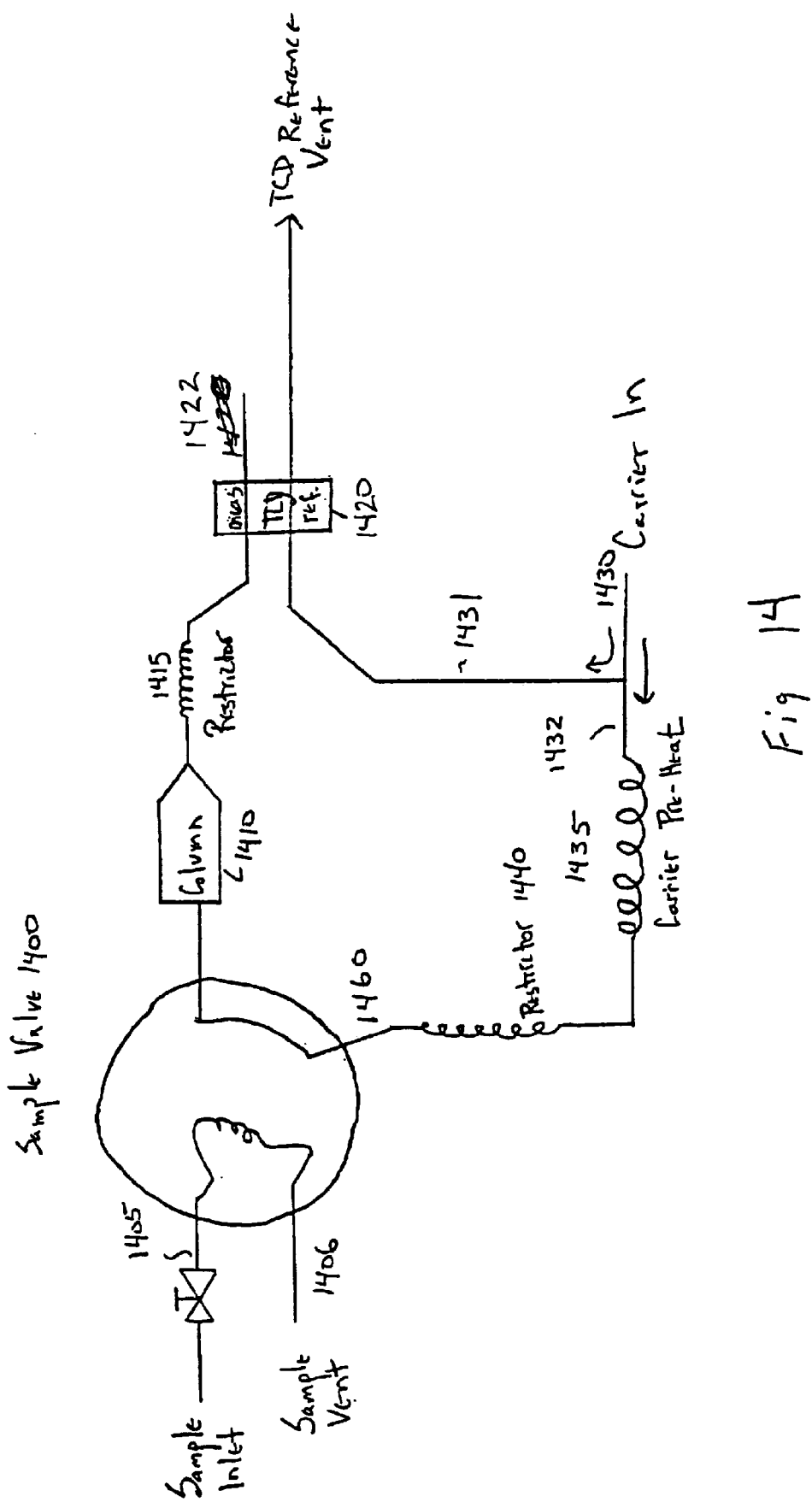
FIG. 14 is a schematic of a fourth embodiment of the invention.

FIG. 14 is the system of FIG. 11 with the addition of a back pressure restrictor upstream of the column. FIG. 14 shows a second embodiment of the invention for a temperature programmed application. A sample valve 1400 attaches to sample-in line 1405 and sample exhaust line 1406. Sample valve 1400 also attaches to carrier-in line 1460 on an upstream side, and column 1410 on a downstream side. Column 1410 attaches to restrictor 1415 on the downstream side, which, in turn, connects to the measurement line 1422 of TCD 1420. First carrier-in line 1430 splits into two carrier streams. First carrier tubing 1431 serves as the reference line for the TCD 1420. Second carrier tubing 1432 coils along its length, resulting in a carrier pre-heat location 1435 in a temperature oven. Downstream of carrier pre-heat location 1435 is a restrictor 1440. Restrictor 1440 connects to the carrier-in line 1460.

One important aspect of the pictured embodiment is the use of a backpressure restrictor upstream of the columns, and preferably upstream of the sample valve. Where the gas chromatograph includes more than one sample valve connected serially, it is preferred to place the backpressure restrictor upstream of all the sample valves, although this is not thought to be necessary to receive some benefit. The preferred backpressure restrictor is what is commonly termed capillary tubing (although capillary tubing is presently used for other purposes, such as a flame restrictor downstream of the column). To make the capillary tubing an effective backpressure restrictor, the ratio of the outlet pressure to the inlet pressure should be less than about 0.528. In other words, $$\frac{P_o}{P_i} \leq 0.528 \quad (6)$$

where,
P$_i$=inlet pressure; and
P$_o$=outlet pressure.

The interpretation of the term "about" is dictated by the purpose of the 0.528 pressure ratio. When the upstream to downstream pressure ratio is less than 0.528, critical (laminar) flow is achieved for the gas flowing through the capillary tubing. Laminar flow is a stable flow profile having a greater flow velocity at its center than at the tubing walls. More important to the invention is a second aspect of critical flow, a constant mass flow. In other words, despite changes in temperatures of 5–10° C. and changes in pressure of five psig (pounds per square inch gauge), the mass flow rate of gas to the column or columns downstream does not vary with any great significance. Even for temperature and pressure fluctuations beyond this range, the mass flow rate varies much less than it would otherwise. Thus, the use of capillary tubing regulates the mass flow provided to the detectors (such as TCD's) in the gas chromatograph and thereby increases the accuracy and reproducibility of the measurements in the gas chromatograph.

Capillary tubing is defined by its small inner diameter, which at maximum is 0.04" inner diameter. The pressure drop through the capillary tubing may be controlled either by adjusting the length or the inner diameter of the tubing. A longer length of tubing results in a greater pressure loss, as does a smaller inner diameter. Capillary tubing may have a 0.0625" outer diameter with a 0.004" to 0.04" inner diameter. Thus, for a given desired pressure drop, a shorter length of tubing is necessary. However, it should be noted that if the sample is not clean, particulates may be carried through the system and such particulates are more likely to plug small tubing than larger tubing. One envisioned embodiment of the invention would include 100 centimeters of 0.01-inch inner diameter tubing. Another has 20 centimeters of 0.05-inch inner diameter tubing. Larger tubing may also be selected, even beyond the range of what is generally considered capillary tubing. However, the resulting length of tubing larger than capillary tubing would generally be undesirably long, and the tubing inner diameter should not be so large as to destroy the tubing's function as a backpressure restrictor.

Another beneficial aspect to placing the pre-heat coil upstream of the backpressure restrictor is to maximize the time the fluid sample resides in the pre-heat coil. In other words, because the capillary tubing limits the maximum mass flow rate through the tubing, the gas flow upstream of the capillary tubing does not flow freely. What results is a longer residence time for the sample in the pre-heat coil. This extra time allows the sample to be heated more reliably and consistently to the desired temperature, improving the reproducibility and accuracy of the gas chromatograph in another way.

By placement of a backpressure restrictor at the column output, an increase of pressure at the column output is achieved. This results in a column pressure ratio p$_i$/p$_o$ more closely approaching unity. The maximum effective distance for placing a backpressure restrictor can be estimated using the following expression:

Distance downstream (cm)=drift time (seconds)*carrier velocity (cm/second)

In a process GC, the peaks of the heavier components in a chromatogram may shift approximately 5–6 seconds across the range of ambient temperature. A reasonable goal is to reduce this peak shifting by an order of magnitude (i.e. 0.5–0.6 seconds), through minimizing longitudinal diffusion and resistance to mass transfer in the mobile phase as discussed previously. At the optimum practical carrier velocity of approximately 35–40 cm/s, (1.5–2 times the theoretical optimum carrier velocity), the maximum distance to achieve this goal is calculated to be about nine inches. A maximum of ten inches is realistic. These distances are generic for any diameter tubing so long as the optimum practical carrier velocity is used.

Various benefits stem from these improvements. First and foremost, the efficiency of a gas chromatograph is improved. The disclosed arrangements and variations thereto also allow the elimination of complicated column treating and cooling equipment previously required for temperature programming.

In process chromatography, it is important to have short analysis times to provide adequate process control. By improving the column efficiency, shorter columns can complete the desired separation resulting in faster analysis times. This technique has the added benefit of being simple and inexpensive to manufacture. The capillary restrictors are study and not prone to breakage. In addition, because capillary tubing is readily available and is inexpensive, rapid acceptance by the industry is expected.

Many variations of the above teachings are within the scope of the invention. For example, any of the embodiments of the invention may advantageously be combined with any other. Multiple sample valves and columns may be used in a single gas chromatograph, or in multiple gas chromatographs used in conjunction. In addition, different backpressure restrictors may be utilized, such as sintered metal discs, inert packed tubing or needle valves. Other temperature detectors may also be used.

What is claimed is:

1. A gas chromatograph, comprising:
   a column to separate components of a fluid sample in a fluid stream;
   a valve switch connected upstream of said column, said valve switch also being connected downstream of a sample source, and downstream of a carrier gas source;
   a backpressure restrictor, upstream of said column, that has an input side and an output side, said backpressure restrictor being suitable to maintain a ratio for a fluid pressure on said output side to a fluid pressure on said input side of less than or equal to about 0.528;
   a first heater for heating said column to a first desired temperature;
   a second heater for heating a carrier gas stream from said carrier gas source to a second desired temperature,
   wherein said second desired temperature is about five to ten degrees Celsius higher than said first desired temperature.

2. The gas chromatograph of claim 1, wherein said back pressure restrictor is capillary tubing.

3. The gas chromatograph of claim 1, wherein said back pressure restrictor is upstream of said valve switch and downstream of said carrier gas stream.

4. The gas chromatograph of claim 3, wherein said back pressure restrictor is capillary tubing.

5. A gas chromatograph, comprising:

a column to separate components of a fluid sample in a fluid stream;

a valve switch connected upstream of said column, said valve switch also being connected downstream of a sample source, and downstream of a carrier gas source;

a backpressure restrictor, upstream of said column, that has an input side and an output side, said backpressure restrictor being suitable to maintain a ratio for a fluid pressure on said output side to a fluid pressure on said input side of less than or equal to about 0.528;

a first heater for heating said column to a first desired temperature;

a second heater for heating a carrier gas stream from said carrier gas source to a second desired temperature, wherein said second temperature is at least 5 degrees Celsius above said first temperature.

6. The gas chromatograph of claim 1, further comprising:

means for cooling said carrier gas stream to a third desired temperature.

7. The gas chromatograph of claim 1, further comprising a housing surrounding said second heater.

8. The gas chromatograph of claim 7, wherein said gas chromatograph further includes in said housing a means for cooling said carrier gas stream.

9. The gas chromatograph of claim 1, wherein second heater heats said carrier gas stream to a series of predetermined temperatures according to a temperature program.

10. The gas chromatograph of claim 1, further comprising:

an effective back pressure restrictor upstream of said column.

11. The gas chromatograph of claim 1, further comprising:

an effective back pressure resistor upstream of said valve switch.

12. The gas chromatograph of claim 1, further comprising:

a second back pressure restrictor downstream of said column.

13. The gas chromatograph of claim 12, further comprising:

an effective back pressure restrictor upstream of said column.

14. The gas chromatograph of claim 12, further comprising:

an effective back pressure restrictor upstream of said valve switch.

15. The gas chromatograph of claim 1, further comprising:

at least a second valve switch;

a back pressure restrictor upstream of all valve switches in said gas chromatograph.

* * * * *